US00PP08942P

United States Patent [19]

Olesen et al.

[11] Patent Number: Plant 8,942

[45] Date of Patent: Oct. 18, 1994

[54] MINIATURE ROSE PLANT NAMED 'POULNYE'

[75] Inventors: Mogens N. Olesen; Pernille Olesen, both of Fredensborg, Denmark

[73] Assignee: Bear Creek Gardens, Inc., Medford, Oreg.

[21] Appl. No.: 96,697

[22] Filed: Jul. 23, 1993

[51] Int. Cl.[5] ..... A01H 5/00

[52] U.S. Cl. ..... Plt./9

[58] Field of Search ..... Plt. 9, 7.1

*Primary Examiner*—Howard J. Locker

*Attorney, Agent, or Firm*—Klarquist Sparkman Campbell Leigh & Whinston

[57] ABSTRACT

A rose plant of the miniature class, a sport of the variety POULvic, having a different flower color from its parent.

1 Drawing Sheet

The present invention relates to a new and distinct variety of rose plant of the miniature class which was discovered by us as a mutation of the variety POULvic, U.S. Plant Pat. No. 8,012.

This variety is unique and distinct from its parent variety, POULvic, principally in its flower color. Instead of having petals that are of Red Group 45C color, the petals are Purple-Red Group 62B on their upper sides and Purple-Red Group 62C on their reverse sides.

Asexual reproduction of this new variety by softwood cuttings, as performed at Somis, Calif., and Fredensborg, Denmark, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Classification:

*Botanical.*—*Rosa hybrida.*

*Commercial.*—Miniature.

FLOWER

Observations made from specimens grown in a greenhouse environment at Fredensborg, Denmark, in 1991.

Blooming habit: Continuous.

Bud:

*Size.*—2 cm long when the petals start to unfurl.

*Form.*—Very long, pointed ovoid.

*Color.*—When sepals first divide, bud color is Red-Purple Group 62B. When half blown, the upper and lower sides of the petals are Red-Purple Group 62C.

*Sepals.*—Color: Green. Surface texture: Covered in fine hairs. There are three normally appendaged sepals. There are two unappendaged sepals with hairy edges.

*Receptacle.*—Color: Green Group 138B. Shape: Apple. Size: Small. Surface: Smooth.

*Peduncle.*—Length: Long. Surface: Prickly. Color: Light green. Strength: Erect.

Bloom:

*Size.*—Medium, for a 10 cm pot rose. Average open size is 4 cm in diameter.

*Borne.*—Several together, in pyramidal clusters averaging 3 to 7 flowers.

*Stems.*—Medium (Average length 15 to 18 cm.); strong.

*Form.*—When first open: Cupped. Permanence: Flattens, outer petals curl back, outer petal edges slightly curled.

*Petalage.*—Number of petals under normal conditions: 30 to 40.

*Color.*—The upper side of the petals is Red-Purple Group 62B. The reverse side of the petals is Red-Purple Group 62C. The bases of the petals are Yellow Group 4D. The major color on the upper side is Red-Purple Group 62B.

*Variegations.*—None.

*Discoloration.*—No change in the general tonality at the end of the first day. At the end of the third day, there is a slight change to Red-Purple Group 62C.

*Fragrance.*—Slight.

Petals:

*Texture.*—Thick.

*Shape.*—Pointed.

*Form.*—Tips slightly recurved, edges slightly quilled.

*Arrangement.*—Informal, with many small petaloids in the center.

*Persistence.*—Drop off cleanly.

*Lastingness.*—On the plant: Very long (10 to 12 days). As a cut flower: Very long (12 days).

Reproductive parts:

*Anthers.*—Size: Medium, if present. Quantity: Often few or none present. Color: Yellow. Arrangement: Mixed with petaloids.

*Filaments.*—Color: Yellow.

*Pollen.*—Color: Lemon yellow.

*Styles.*—Color: Light green.

*Stigmas.*—Color: Greenish white.

Form: Bush.

Growth: Dwarf, upright. Average height of the miniature pot rose is less than 25 cm.

Foliage:

*Number of leaflets on normal mid-stem leaves.*—5.

*Size.*—Small.
*Quantity.*—Normal.
*Color.*—New foliage: Top: RHS Green Group 138B; reverse: RHS Green Group 138C. Old foliage: Green Group 137A.

Leaflets:
*Shape.*—Oval pointed.
*Texture.*—Upper side: Leathery, smooth.
*Edge.*—Serrated.
*Serration.*—Single, small.
*Petiole rachis.*—Color: Green.
*Petiole underside.*—Smooth.
*Stipules.*—Medium.
*Disease resistance.*—Resistant to mildew and black-spot under normal greenhouse conditions.

Wood:
*New wood.*—Color: Light green. Bark: Smooth.
*Old wood.*—Color: Green. Bark: Smooth.

Prickles:
*Quantity.*—On main canes from base: Ordinary. On laterals from main canes: Ordinary.
*Form.*—Straight.
*Color when young.*—Green at base shading to red at tip. Translucent.

Small prickles:
*Quantity.*—On main stalks: Many. On laterals: Few.
*Color.*—Green.

We claim:

1. A new and distinct variety of rose plant of the miniature class, substantially as herein shown and described, a sport of the variety POULvic, U.S. Plant Pat. No. 8,012, characterized particularly as to novelty by its difference in flower color from its parent.

* * * * *

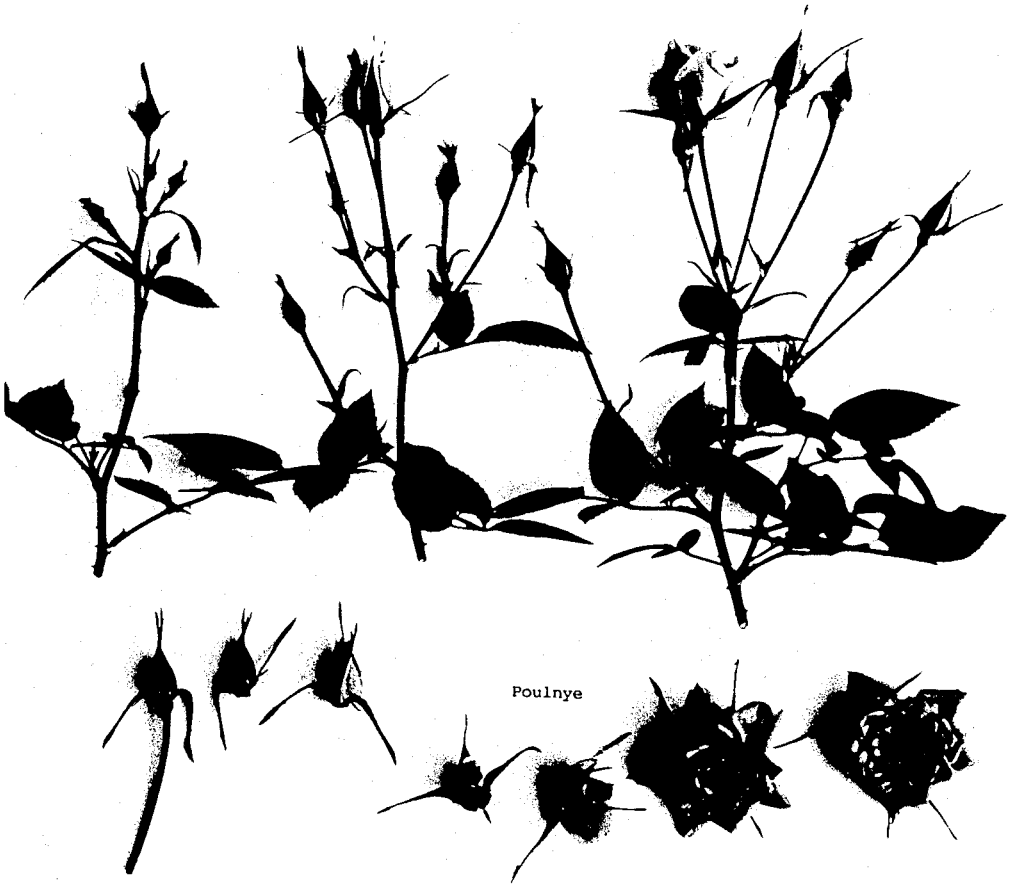
Poulnye